United States Patent
Hofmann et al.

(10) Patent No.: US 6,821,777 B2
(45) Date of Patent: Nov. 23, 2004

(54) CELL LINE PREPARING AND PRODUCING OVINE ADENOVIRUS VECTORS

(75) Inventors: Christian Hofmann, Berlin (DE); Moritz Hillgenberg, Berlin (DE); Peter Löser, Berlin (DE)

(73) Assignee: DeveloGen Aktiengesellschaft für entwicklungsbiologische Forschung, Göttingen (DE)

( * ) Notice: Subject to any disclaimer, the term of this patent is extended or adjusted under 35 U.S.C. 154(b) by 80 days.

(21) Appl. No.: 10/181,214

(22) PCT Filed: Jan. 12, 2001

(86) PCT No.: PCT/EP01/00366

§ 371 (c)(1),
(2), (4) Date: Jul. 15, 2002

(87) PCT Pub. No.: WO01/51606

PCT Pub. Date: Jul. 19, 2001

(65) Prior Publication Data

US 2003/0003566 A1 Jan. 2, 2003

(30) Foreign Application Priority Data

Jan. 14, 2000 (DE) .......................... 100 01 390

(51) Int. Cl.⁷ .............................. C12N 5/00; C12N 5/06
(52) U.S. Cl. ..................................... 435/325; 424/233.1
(58) Field of Search ..................... 435/325; 424/233.1

(56) References Cited

FOREIGN PATENT DOCUMENTS

| AU | WO 96/03508 | * | 2/1996 |
| WO | WO 96 03508 | | 2/1996 |

OTHER PUBLICATIONS

Xu, Z.Z. Und Both, G. W.: "Altered tropism of an ovine adenovirus carrying the fiber protein cell binding domain of human adenovirus type 5" Virology, vol. 248, Aug. 15, 1998, pp. 156–163, XP000985985; the whole document.

Well, D.N. et al.: "Production of cloned lambs from an established embryonic cell line: A comparison between in vivo– and in vitro–matured cytoplasts" Biology Of Reproduction, vol. 57, 1997, pp. 385–393, XP002067037; p. 386, left–hand column, line 6—line 39.

Pye, D.: "Cell lines for growth of sheep viruses" Australian Veterinary Journal, vol. 66, 1989, pp. 231–232, XP000995465 cited in the application The whole document.

\* cited by examiner

*Primary Examiner*—James C. Housel
*Assistant Examiner*—Stacy B. Chen
(74) *Attorney, Agent, or Firm*—Rothwell, Figg, Ernst & Manbeck, P.C.

(57) ABSTRACT

The invention relates to the ovine embryo cell line HVO-156 (DSM ACC2440), or to cell lines derived therefrom, and to their use for preparing and propagating ovine adenoviruses, in particular recombinant ovine adenoviruses which are derived from the isolate OAV 287.

5 Claims, 3 Drawing Sheets

CELL LINE PREPARING AND PRODUCING OVINE ADENOVIRUS VECTORS

DESCRIPTION

Figure 1:
Figure 1:

The invention relates to the ovine embryo cell line HVO-156 (DSM ACC2440), or to cell lines derived therefrom, and to their use for preparing and propagating ovine adenoviruses, in particular recombinant ovine adenoviruses which are derived from the isolate OAV 287.

Genetic defects can cause diseases, such as cancer, cystic fibrosis, muscular dystrophy and others. A large number of gene therapy methods have already been proposed for remedying these genetic defects. Methods for preparing vectors which are able to introduce therapeutic genes into the genetically defective target cells with an adequately high efficiency constitute the basis for a successful gene therapy.

The ability of viruses, which is highly developed from the evolutionary point of view, to introduce genetic material into mammalian cells suggests that viral vectors should be used for gene therapy. Thus far, it is first and foremost human viruses having low pathogenic potential, such as attenuated adenoviruses, adenoassociated viruses, herpesviruses and retroviruses, which have been employed as vectors. In connection with this, it has been recognized that none of the systems mentioned can be used for any gene therapy applications. In general, an immunity which preexists endemically in most people, and which was elicited by an infection with these viruses in childhood, suggests that it will not be possible to use human viral vectors successfully in humans.

Viral vectors which are able to overcome this preexisting immunity in humans are based, inter alia, on ovine adenoviruses, in particular the ovine adenovirus isolate OAV 287. This virus, and the use of recombinant variants of the virus for gene therapy, is described in WO96/03508 and WO97/06826. However, problems have thus far been associated with preparing and propagating viruses of this nature. The ovine lung cell line CSL 503 (Pye et al., Austr. Vet. J. 66: 231–232 (1989)), which is at present the only cell line available for this purpose, is not particularly efficient. Thus, only a small number of recombinant ovine adenoviruses are formed when this cell line is transfected with recombinant ovine adenovirus DNA. In addition to this, the cell line CSL 503 only has a relatively short life span of what is normally less than 20 passages and therefore only allows viruses to be replicated at a comparatively low rate.

There therefore exists a need to provide alternative cell lines which have a higher efficiency for preparing adenoviruses. It has been found that ovine embryo cell lines, in particular the ovine embryo cell line HVO-156 (DSM ACC2440), or cell lines derived therefrom, enable adenoviruses to be propagated with such a degree of efficiency. These cells are distinguished by a long life span (the ability to be passaged at least 40 times, corresponding to >100 generations), the ability to be readily transfected with recombinant DNA, a high degree of efficiency in the formation of recombinant ovine adenoviruses and a high rate of propagation of recombinant ovine adenoviruses.

The invention consequently relates to the ovine embryo cell line HVO-156 (DSM ACC2440) or to a cell line which is derived therefrom. This cell line was deposited in the DSMZ (Deutsche Sammlung von Mikroorganismen und Zellkulturen GmbH [German collection of microorganisms and cell cultures GmbH]), Mascheroder Weg 1b, D-38124, Braunschweig, in accordance with the provisions of the Budapest treaty, on Dec. 22, 1999.

The deposited cell line, or cell lines which are derived therefrom, for example by subcloning, and also other ovine embryo cell lines, are suitable for preparing and/or propagating adenoviruses, in particular ovine adenoviruses, such as ovine adenoviruses of the isolate OAV 287 and recombinant viruses which are derived therefrom.

In addition, the invention will be explained by the following figures and examples.

Figure 2:
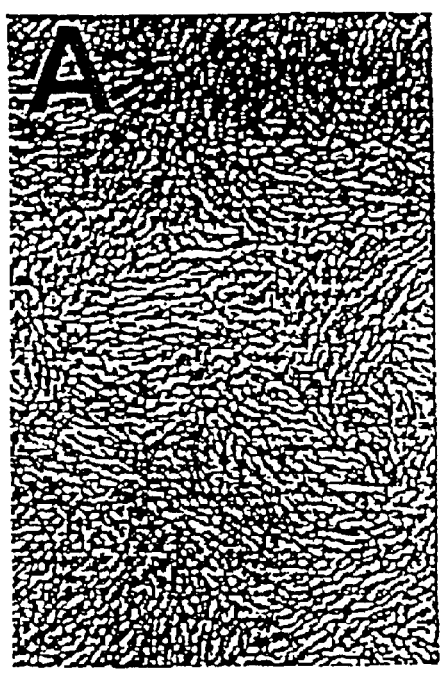
Figure 2:
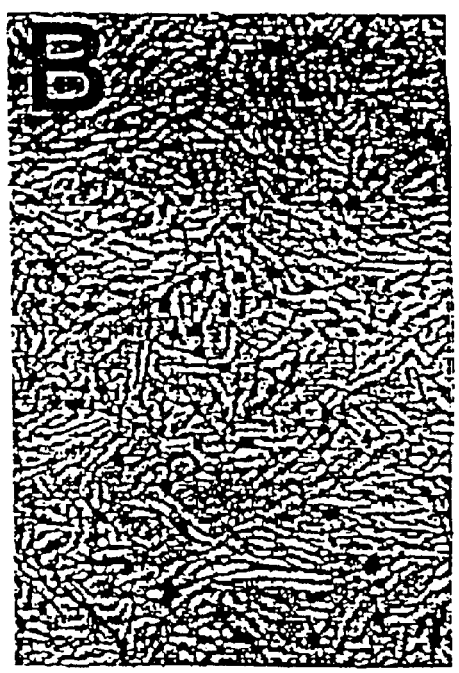

FIG. 1: shows the morphology of HVO-156 cells (DSM ACC2440) before culturing (A) and after culturing for 40 passages (B), FIG. 2: shows the efficiency with which a plasmid is transfected into HVO-156 cells using lipofection: (A) mock transfection, (B) transfection with plasmid, and FIG. 3: shows the efficiency with which a recombinant ovine adenovirus is produced in HVO-156 cells.

EXAMPLE 1

HVO-156 cells were cultured at 37 (or 40) ° C., for up to 40 passages, in DMEM. The cells were analyzed morphologically before and after culturing. No differences were found in the morphological appearance, as can be seen from comparing FIGS. 1A (morphology before culturing) and 1B (morphology after 40 passages).

EXAMPLE 2

2 µg of the plasmid pRSVβgal bpA (Hofmann et al., Proc. Natl. Acad. Sci, USA 92 (1995), 10099–10103), containing a lacZ-Expression cassette, were transfected into HVO-156 cells by means of lipofection (Lipofectamine, Gibco). After 48 hours, the expression of lacZ was detected histologically by staining the cell nuclei blue following the lacZ-mediated conversion of substrate. FIG. 2A shows a mock transfection. After the dark cell nuclei in FIG. 2B have been counted, the lipofection is seen to give a transfection efficiency of approx. 80%.

EXAMPLE 3

5 µg of the linearized genomic DNA of the recombinant ovine adenovirus pOAVhAAT (Hofmann et al. (1999), J. Virol. 73, 6930–6936) were transfected by means of lipofection into HVO-156 cells and the efficiency of the formation of recombinant ovine adenoviruses was determined. Five recombinant viruses were found in six rescue experiments.

This is a very high efficiency since only one recombinant virus is found, in an average of 8 transfection experiments carried out under comparable conditions, in the case of the cell line CLS 503.

EXAMPLE 4

The quantity of OAVHAAT recombinant ovine adenoviruses (Hofmann et al. (1999), J. Virol. 73, 6930–6936) produced in HVO-156 cells was analyzed in dependence on the quantity of virus which was initially employed. $3 \times 10^5$ cells were infected at MOIs (multiplicities of infection) of 0.2/2/10 and the titer of the total virus produced was determined after 48 hours using an end point dilution assay, as described in Hofmann et al. above.

Figure 3:
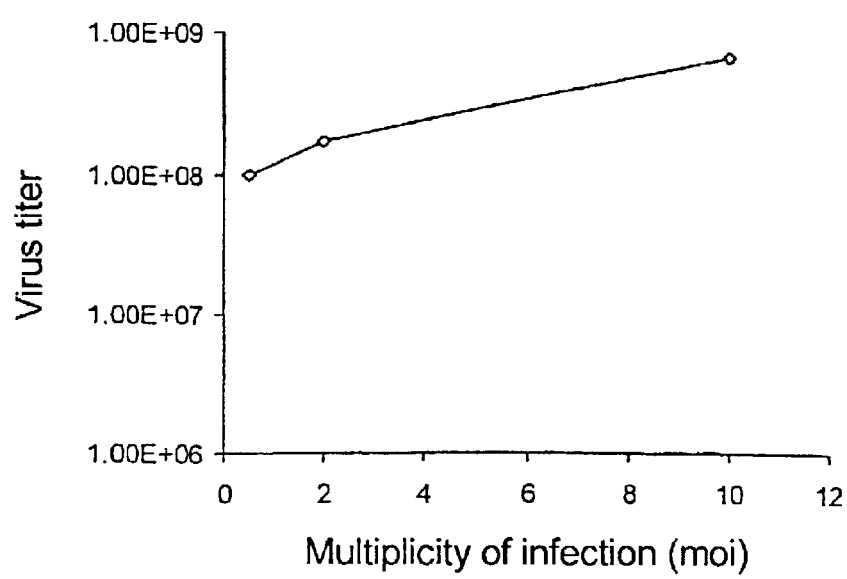

The quantity of virus which was produced per cell can be seen from FIG. 3. At an MOI of 2, the quantity of virus which was produced was approx. $1.4 \times 10^4$ infectious particles per cell.

FIG. 1:

HVO-156 A) before and B) after 40 passages No change can be seen in the cell line after 40 passages.

FIG. 2:

Efficiency with which HVO-156 cells are transfected A) mock-transfected B) transfected with plasmid pRSVβgalbpA Counting (dark nuclei) gave a transfection of 80%.

FIG. 3:

Efficient production of OAVhaat by HVO-156 cells. $3 \times 10^5$ cells were infected at the given moi and the number of viruses produced was determined. The determination is effected using an end point dilution assay.

At an moi of 2, the quantity of virus produced per cell was approx. $1.4 \times 10^4$ infectious particles per cell.

What is claimed is:

1. A method for preparing and/or propagating adenoviruses, comprising transfecting ovine embryo cells with recombinant adenovirus DNA, wherein said ovine embryo cells are HVO-156 (DSM ACC 2440) cells, and recovering any recombinant adenoviruses formed.

2. The method according to claim 1, wherein said adenoviruses are ovine adenoviruses.

3. The method according to claim 2, wherein said ovine adenoviruses are OAV 287.

4. The method according to claim 1, wherein said ovine embryo cells have a transfection efficiency of about 80%.

5. An isolated cell line HVO-156 (DSM ACC 2440).

* * * * *